(12) United States Patent
Gagnon

(10) Patent No.: US 9,204,720 B2
(45) Date of Patent: Dec. 8, 2015

(54) RECONFIGURABLE FURNITURE

(71) Applicant: Shane Joseph Gagnon, Bradford (CA)

(72) Inventor: Shane Joseph Gagnon, Bradford (CA)

( * ) Notice: Subject to any disclaimer, the term of this patent is extended or adjusted under 35 U.S.C. 154(b) by 221 days.

(21) Appl. No.: 13/656,967

(22) Filed: Oct. 22, 2012

(65) Prior Publication Data

US 2013/0102842 A1   Apr. 25, 2013

Related U.S. Application Data

(60) Provisional application No. 61/627,893, filed on Oct. 20, 2011.

(51) Int. Cl.
| | |
|---|---|
| *A47B 85/00* | (2006.01) |
| *A47B 87/00* | (2006.01) |
| *A61F 5/01* | (2006.01) |
| *A47C 3/16* | (2006.01) |
| *A47C 13/00* | (2006.01) |
| *A47C 15/00* | (2006.01) |
| *A47C 16/02* | (2006.01) |

(52) U.S. Cl.
CPC ............... *A47B 87/00* (2013.01); *A47B 85/00* (2013.01); *A47C 3/16* (2013.01); *A47C 13/005* (2013.01); *A47C 15/008* (2013.01); *A47C 16/02* (2013.01); *A61F 5/01* (2013.01)

(58) Field of Classification Search
CPC ........................................................ A47B 85/00
USPC ......... 5/632, 648, 657; 297/119, 129, 423.41, 297/440.14; 108/11–13
See application file for complete search history.

(56) References Cited

U.S. PATENT DOCUMENTS

| | | | |
|---|---|---|---|
| 4,171,549 A | 10/1979 | Morrell et al. | |
| 4,473,913 A | 10/1984 | Ylvisaker | |
| 4,777,678 A * | 10/1988 | Moore | ............................. 5/657 |
| 4,905,330 A | 3/1990 | Jacobs | |
| 5,292,093 A * | 3/1994 | Shumake | ......................... 248/97 |
| 6,925,669 B1 | 8/2005 | Friedman et al. | |

* cited by examiner

*Primary Examiner* — John Lacyk
(74) *Attorney, Agent, or Firm* — Volpe and Koenig, P.C.

(57) ABSTRACT

An article of reconfigurable furniture is provided including a plurality of cushions, at least some of which are generally triangular in cross-section, the cushions being dimensioned to be stackable in a cube. A cube shaped cube cover is provided for covering said cushions when said cushions are stacked into said cube. The cushions are covered by cushion covers having interactive engagement elements for releasably securing said cushions one to another to provide at least one contoured support surface for supporting a user thereon in at least one selected pose.

3 Claims, 10 Drawing Sheets

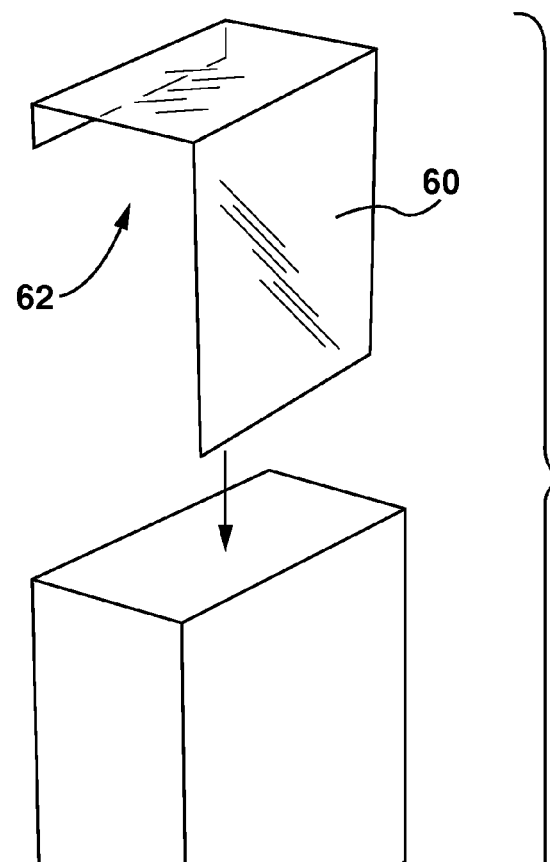
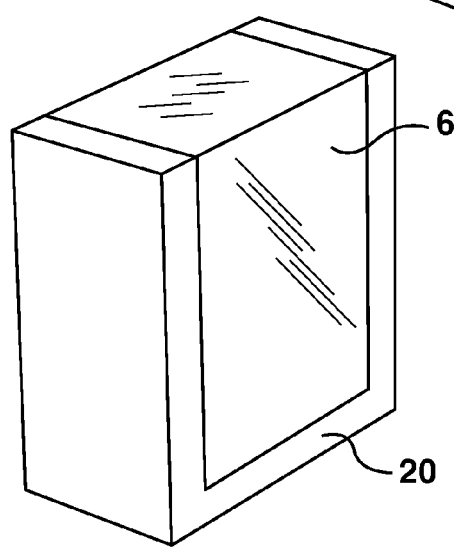
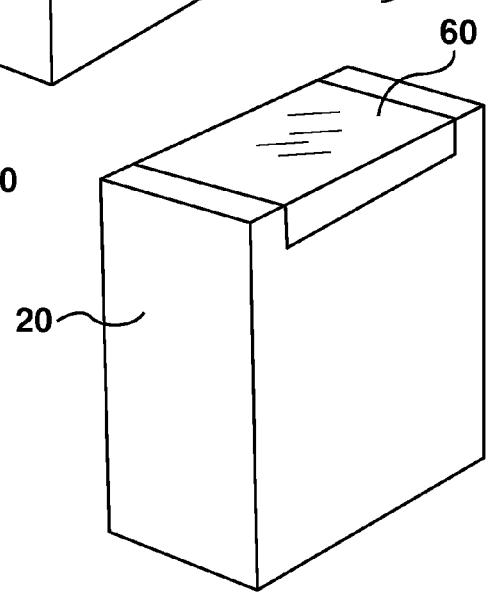
FIG. 4          FIG. 5

RECONFIGURABLE FURNITURE

FIELD OF INVENTION

This invention relates generally to furniture. More particularly, this invention relates to furniture which can be reconfigured to serve different functions.

BACKGROUND OF THE INVENTION

The use of a plurality of different shaped cushions which can be juxtaposed to provide support surfaces with different configurations is described for example in the following U.S. patent references, the disclosures of which are hereby incorporated by reference herein:
U.S. Pat. No. 6,925,669 B1;
U.S. Pat. No. 4,905,330;
U.S. Pat. No. 4,473,913; and,
U.S. Pat. No. 4,171,549.

A problem with such devices is that cushions by their nature tend to be bulky which causes storage issues when they are not being deployed.

SUMMARY OF THE INVENTION

According to the present invention, an article of reconfigurable furniture is provided comprising:
a plurality of cushions, at least some of which are generally triangular in cross-section, said cushions being dimensioned to be stackable in a cube;
a cube shaped cube cover for covering said cushions when said cushions are stacked into said cube;
said cushions being covered by cushion covers having interactive engagement elements for releasably securing said cushions one to another to provide at least one contoured support surface for supporting a user thereon in at least one selected pose.

The cube cover may include a generally rectangular sleeve insertable through an openable face thereof to maintain said cube cover in a box-like configuration for facilitating insertion of said cushions.

The article may include an overlay having a hard surface mountable to said cube cover to convert said cube into a table.

The overlay may have a generally rectangular C-shaped profile defining a channel for receiving said cube.

An adult stimulation device is also provided having: a resilient cushion with a passage extending therethrough;
a penetrating member sized for insertion into a body cavity and extending from a substantially rigid base broader than said passage;
said penetratory member extending form said passage in response to depression of said cushion member about said passage.

The device may include a cushion cover having an aperture registering with said passage through which said member may protrude.

The cushion cover of the device may include interengaging attachment elements for detachable attachment to other cushions covers.

BRIEF DESCRIPTION OF THE DRAWINGS

These and other features of the invention will become more apparent from the following description in which reference is made to the appended drawings wherein:
FIG. 3 is an exploded perspective view illustrating placement of a hard surface overlay over the article of the present invention;
FIG. 4 is a perspective view from above and toward one side of the article with the overlay in place;
FIG. 5 corresponds to FIG. 4 but shows an opposite face of the article.

DETAILED DESCRIPTION OF THE PREFERRED EMBODIMENTS

Figure 1:
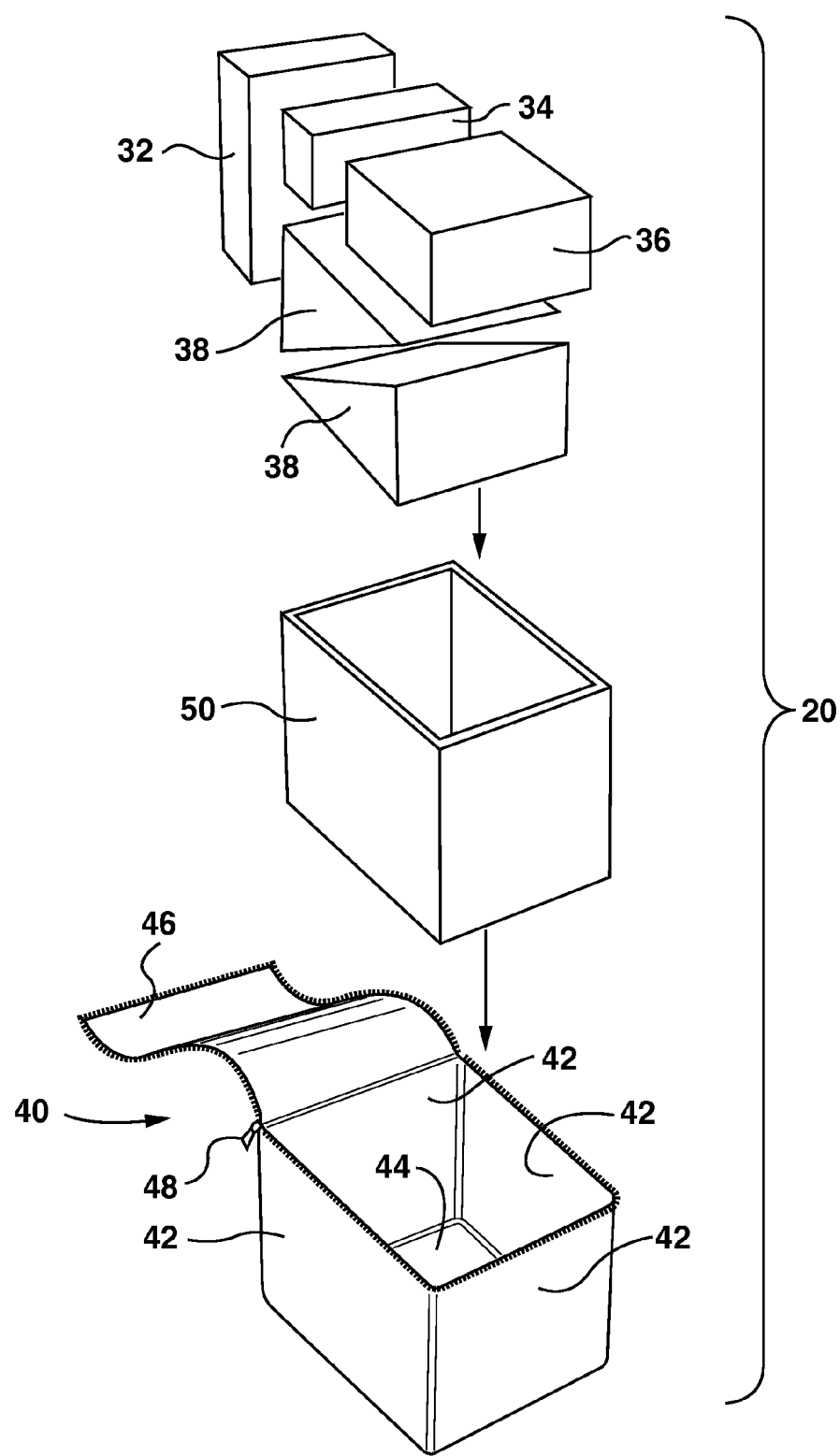
FIG. 1 is an exploded perspective view of an article of reconfigurable furniture according to the present invention.

An article of reconfigurable furniture according to the present invention is generally indicated by reference 20 in the accompanying illustrations. The article 20 comprises a plurality of cushions 32, 34, 36, 38 of different sizes and shapes.

Cushions 32, 34 and 36 are generally rectangular whereas cushions 38 are generally triangular in profile.

The cushions 32, 34, 36 and 38 are stackable to form a cube and may in fact have been cut from a cube of resilient material such as upholstery foam. The term "cube" should be liberally rather restrictively interpreted to include various geometric shapes which can be achieved by stacking smaller units together into a stacked shape which is functionally useful in the same sense as the rectangular cube illustrated. For example, a cube with a trapezoidal profile or other shapes presenting generally flat and parallel upper and lower faces may be contemplated.

The cushions 32, 34, 36 and 38 may be laid out over an underlying surface such as a floor or a mattress to provide a contoured support surface. The support surface is arranged to facilitate whatever pose the user of the device is contemplating. Typical arrangements and poses are well-known, as evidenced for example, by some of the above cited references and accordingly need no further discussion or illustration.

A cube shaped cube cover 40 is provided to cover the cushions 32, 34, 36 and 38 when the cushions are consolidated into the cube shape and to hold them in the consolidated configuration. The cube cover 40 illustrated has four sides faces 42 and a bottom face 44 defining a box-like shape. An upper face 46 acts as an operable top to define an opening in the "box" for receiving the cushions 32, 34 36 and 38. A zipper 48 or other releasable interengaging fastening element may be used to secure the "top" to three of the side faces 42.

A sleeve 50 illustrated having a generally rectangular shape may be provided. The sleeve 50 is sized to conform to the inside of the cube cover 40.

Figure 7:
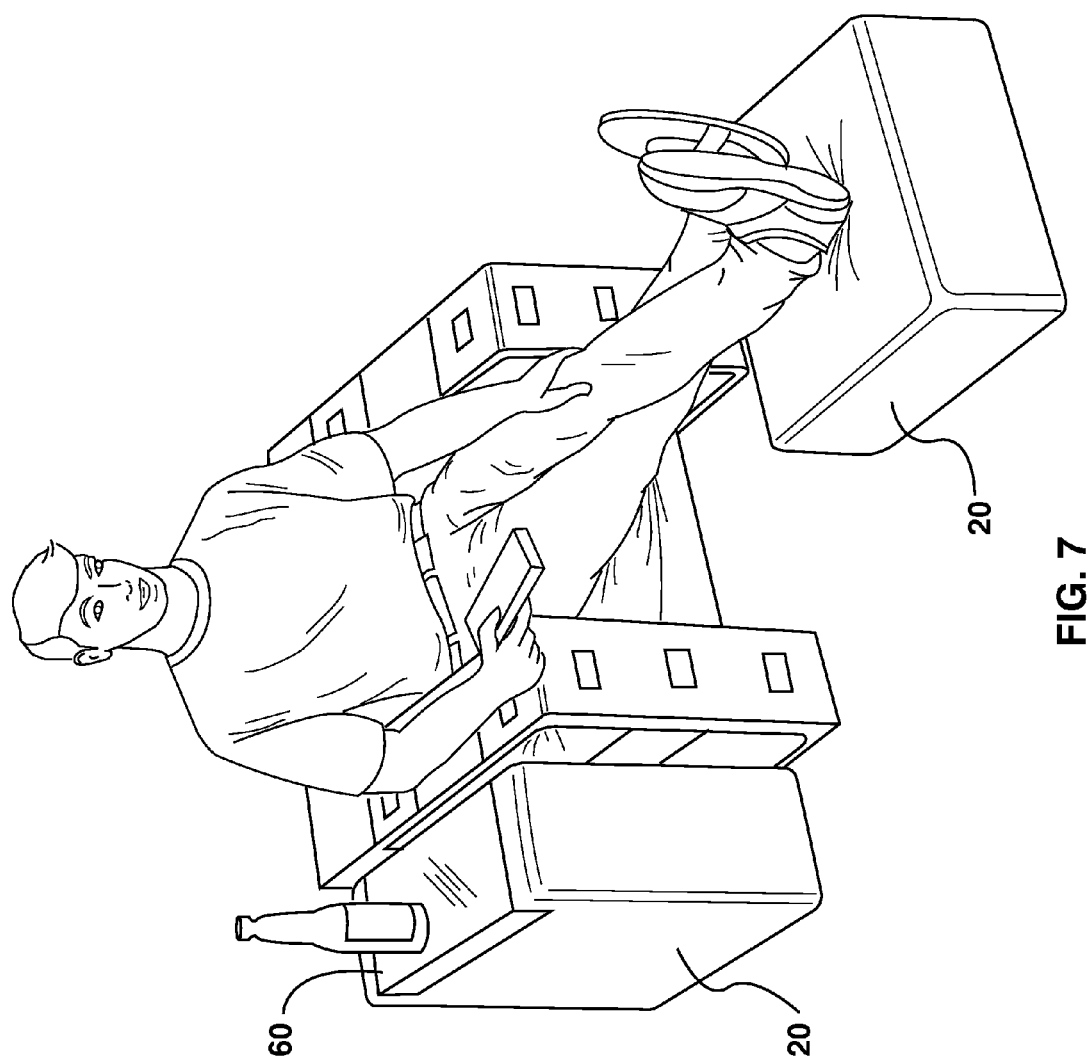
FIG. 7 is a perspective view illustrating an article according to the present invention as a footstool and an article according to an alternate embodiment of the present invention as an end table.
Figure 8:
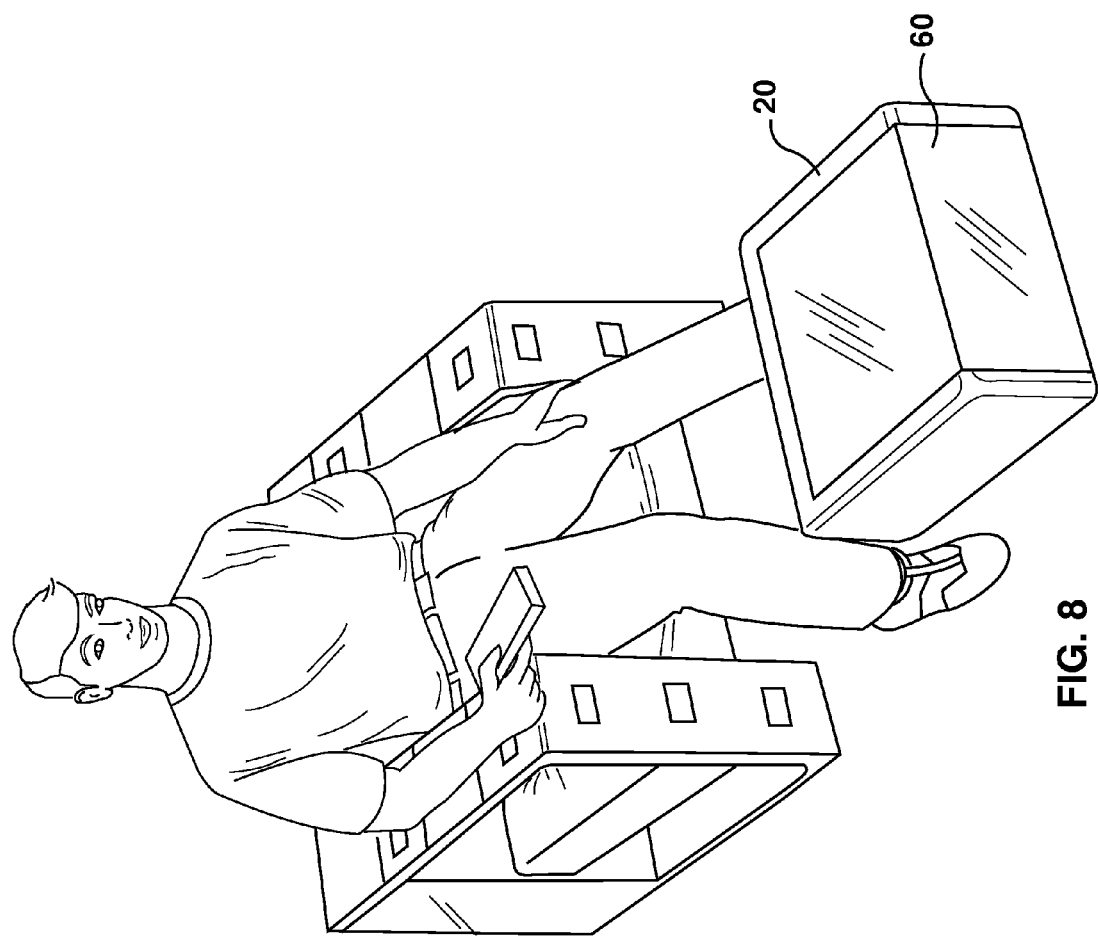
FIG. 8 is a perspective view showing an article according to the present invention in use as a coffee table.
Figure 9:
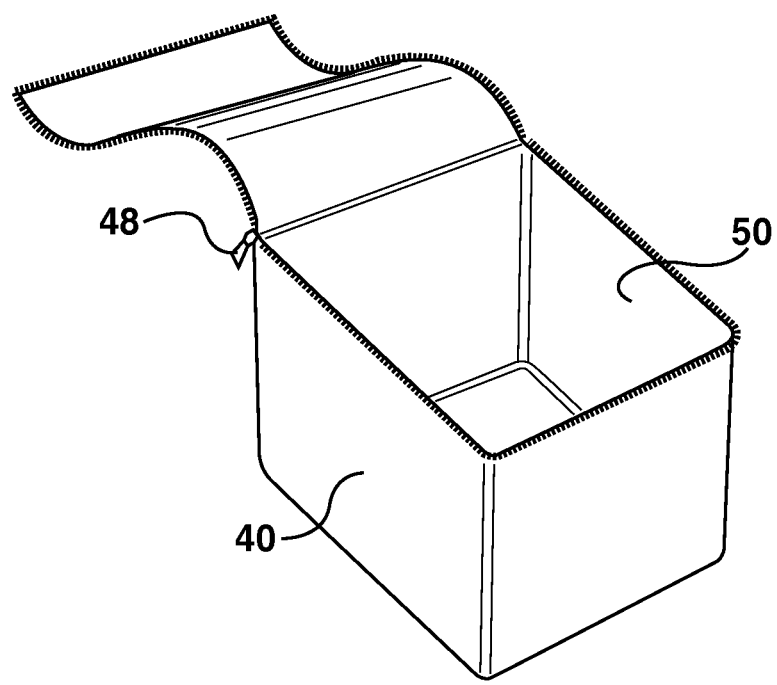
FIG. 9 is a perspective view from above of a cube cover portion of the present invention.

The sleeve 50 is of a rigid or semi-rigid material such as for example cardboard or plastics. The sleeve 50 maintains the shape of the cube cover 40 thereby facilitating insertion and consolidation of the cushions 32, 34, 36 and 38. The sleeve also provides rigidity to the article 50 enabling its use as an end table, footstool or coffee table as shown in FIGS. 7 and 8.

Figure 2:
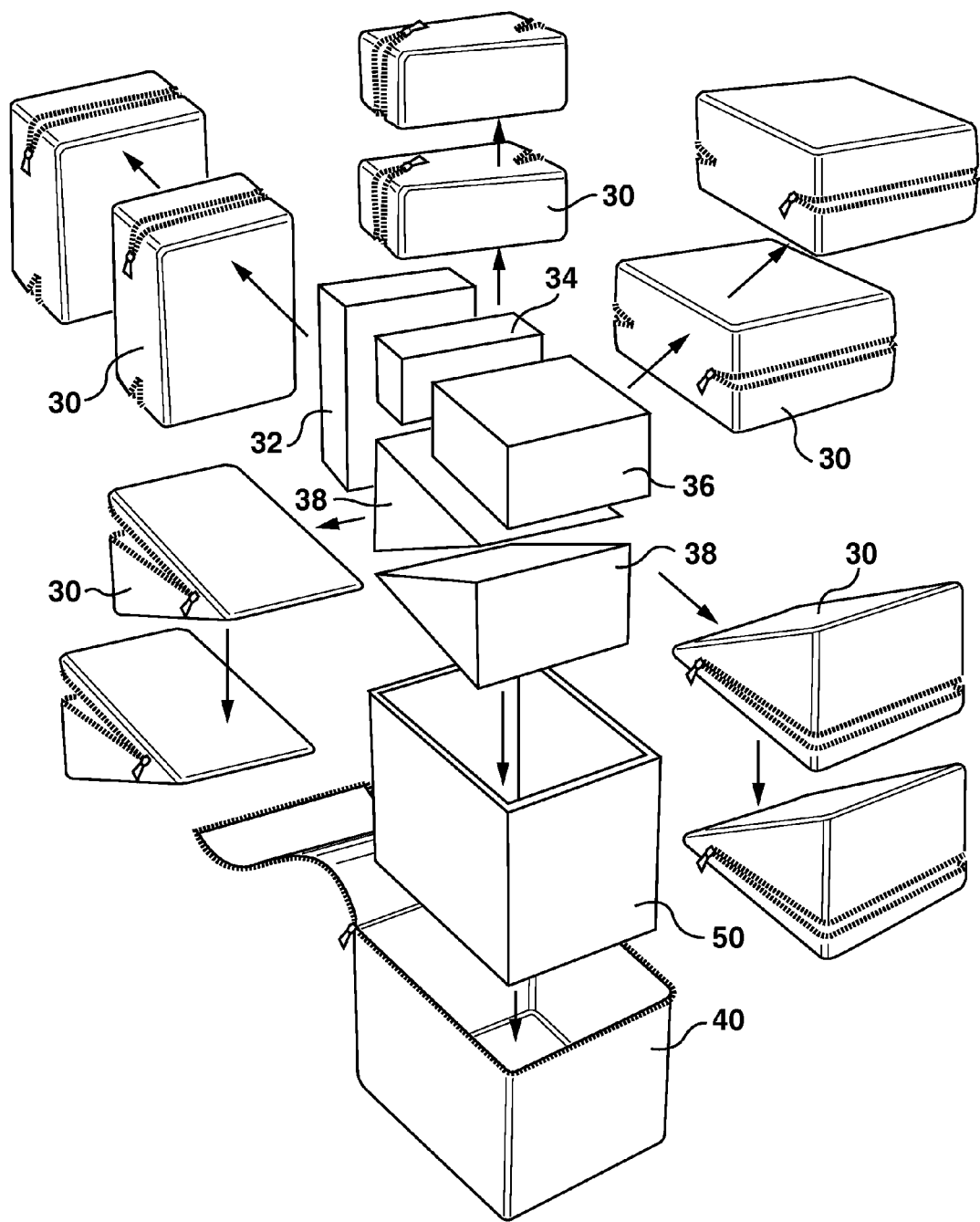
FIG. 2 is a further exploded perspective view of an article of reconfigurable furniture according to the present invention.
Figure 6:
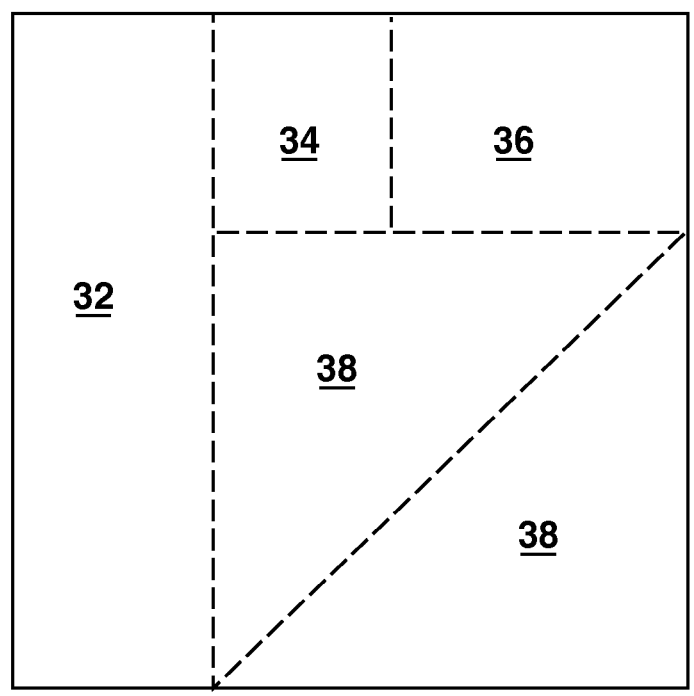
FIG. 6 is an end elevation showing a possible stacking configuration of cushion portions of the article.

The cushions 32, 34, 36 and 38 may be provided with respective cushions covers 30 as shown in FIG. 2. The cushion covers 40 improve the aesthetic and tactile quality of the cushions 32, 34 36 and 38.

The cushion covers 30 may be provided with interactive engagement elements (hook and loop fasteners, snap fasteners, buttons and flaps, ties, etc.) to secure adjacent of the cushions 32, 34, 36 and 38 in whatever arrangement they are put in. The cushion covers 30 may be provided with a flap or other protective means to cover any non-deployed fasteners when such are not in use so as not to irritate a user of the article. The cushion covers 30 may also be provided with orientation means such as colour coding or numbers to facilitate consolidating the individual cushions 32, 34, 36 and 38 into a cube.

A hard surfaced overlay 60, such as illustrated in FIGS. 3, 4 and 5 may be provided to protect the cube cover 40 and as well provide more rigidity when the article is to be used as a table. The overlay 60 may be of transparent or non-transparent plastics material, sheet metal, etc. The overlay 60 may, as illustrated, have a generally rectangular "C" shaped profile defining a channel 62 for receiving the balance of the article 20.

FIGS. 10 through 15 illustrate an adult stimulation device 100 which may be used as one or more of the cushions 32, 34 and 36. The device 100 has a resilient cushion 110 having a passage 120 extending therethrough.

A penetratory member 130 (i.e. a dildo) sized for insertion into a body cavity for sexual stimulation extends form a base 132. The penetratory member 130 is inserted into the passage 120. The base 132 is broader than the passage 120 limiting the depth to which the penetratory member may be inserted.

Figure 10:
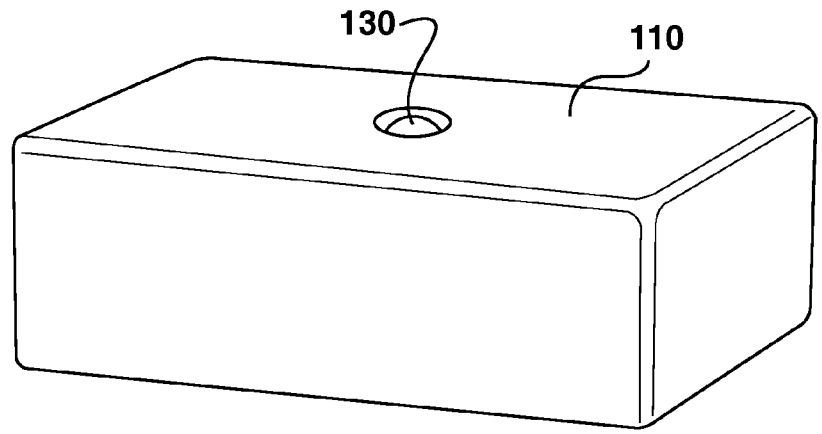
FIG. 10 is a perspective view of an adult stimulation device in accordance with the present invention in a non-deployed configuration.
Figure 11:
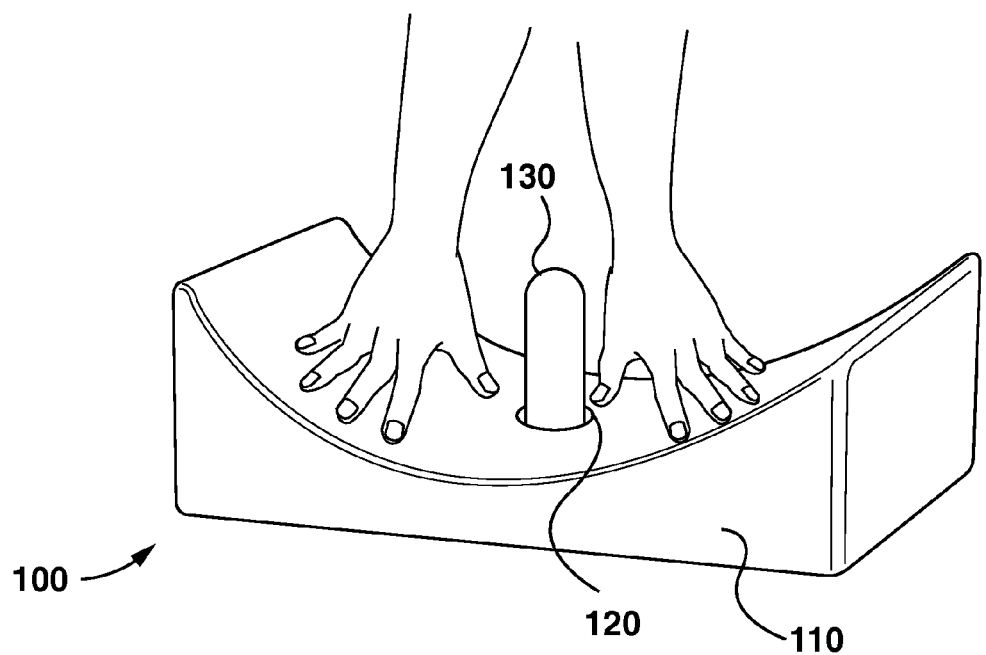
FIG. 11 is a perspective view of the device of FIG. 10 in a deployed configuration.
Figure 12:
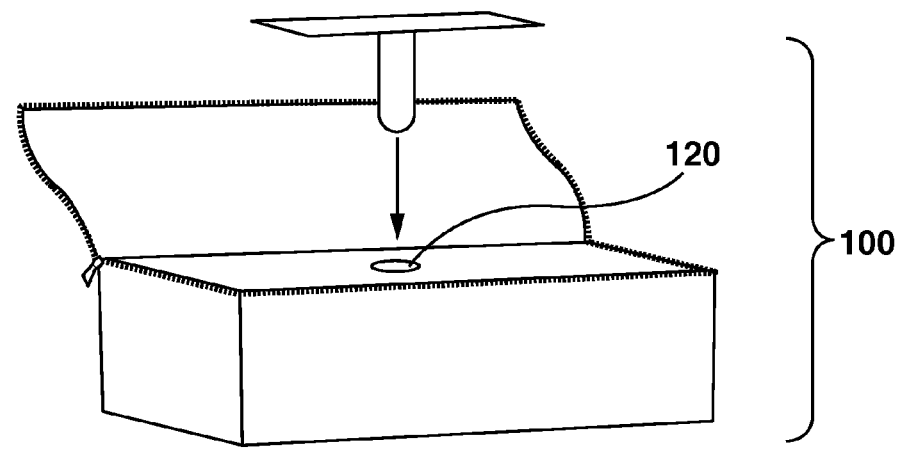
FIG. 12 is an exploded perspective view of the device of FIGS. 10 and 11.
Figure 13:
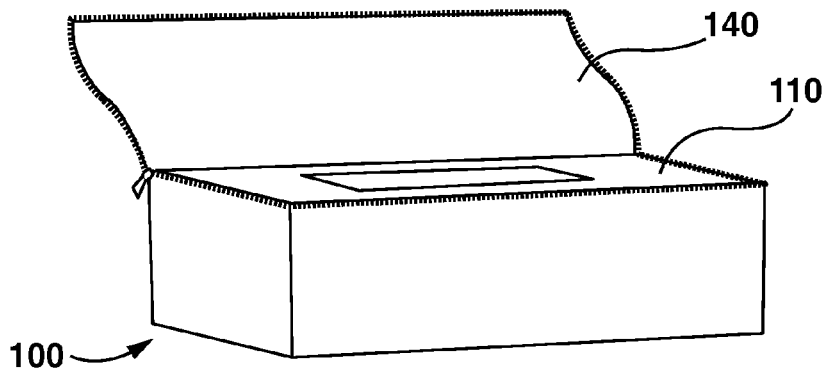
FIG. 13 is a perspective view of the device of FIGS. 10 and 11 with an openable side in an open configuration.
Figure 14:
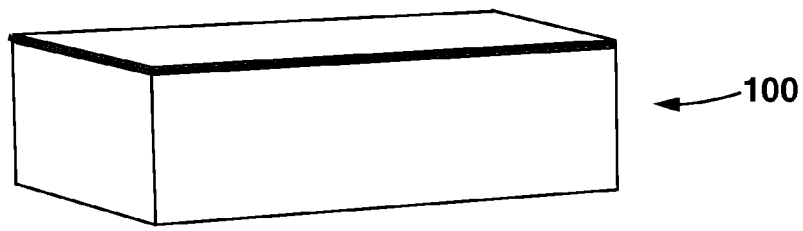
FIG. 14 is a perspective view of the device of FIG. 10 in an inverted configuration; and,
FIG. 15 is a perspective view of a penetratory member and base of the device of FIGS. 11 through 14.
Figure 15:
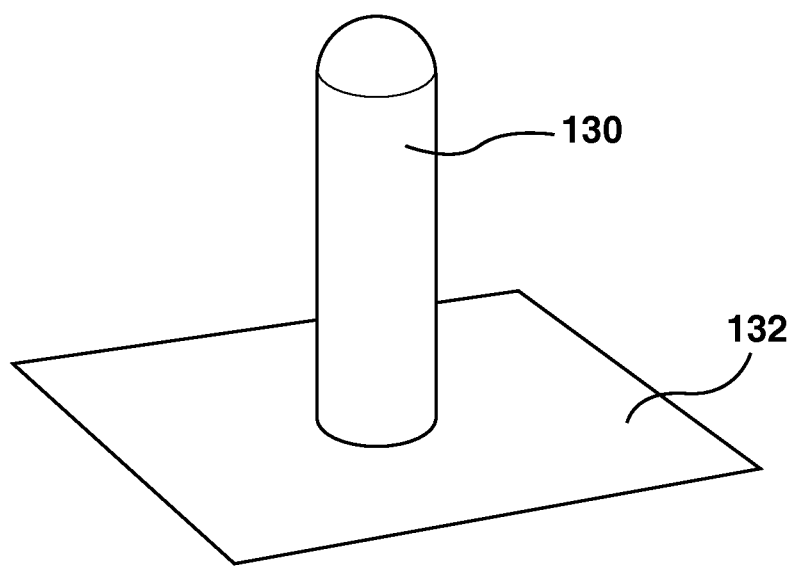

In a non-deployed configuration illustrated in FIG. 10, the penetratory member 130 is generally flush with the cushion 110. Depressing the cushion 110 as shown in FIG. 11 causes the penetratory member to stand proud of (extend from) the cushion member 110. The cushion member 110 provides resiliency and accordingly a user can control depth of penetration by controlling bounce.

Further stimulation may be provided by mechanizing the penetratory member for example to cause it to vibrate, oscillate, etc.

A cushion cover 140 may be provided having an aperture registering with the passage and through which the penetrating member 130 may protrude.

The above description is intended in an illustrative rather than a restrictive sense. Variations to the preferred embodiments described may be apparent to persons skilled in the art without departing from the spirit or scope of the invention as defined by the claims set out below.

I claim:

1. An article of reconfigurable furniture, comprising:
a plurality of cushions, at least some of which are generally triangular in cross-section, said cushions being dimensioned to be stackable in a cube;
a cube shaped cube cover for covering said cushions when said cushions are stacked into said cube;
said cushions being covered by cushion covers having interactive engagement elements for securing said cushions one to another to provide at least one contoured support surface for supporting a user thereon in at least one selected pose; and
an overlay having a hard surface mountable to said cube cover to convert said cube into a table.

2. The article of reconfigurable furniture of claim 1, wherein cube shaped cover includes a generally rectangular sleeve insertable through an openable face thereof to maintain said cube cover in a box-like configuration for facilitating insertion of said cushions.

3. The article of reconfigurable furniture of claim 1, wherein the overlay has a generally rectangular C-shaped profile defining a channel for receiving said cube.

* * * * *